US00PP34065P2

(12) United States Plant Patent
Tamura

(10) Patent No.: US PP34,065 P2
(45) Date of Patent: Mar. 22, 2022

(54) ***GENTIANA* PLANT NAMED 'ASHIRO 272219'**

(50) Latin Name: ***Gentiana* hybrid**
Varietal Denomination: Ashiro 272219

(71) Applicant: Masahiko Tamura, Hachimantai (JP)

(72) Inventor: Masahiko Tamura, Hachimantai (JP)

(73) Assignee: HACHIMANTAI CITY, Hachimantai (JP)

( * ) Notice: Subject to any disclaimer, the term of this patent is extended or adjusted under 35 U.S.C. 154(b) by 0 days.

(21) Appl. No.: 17/197,210

(22) Filed: Mar. 10, 2021

(51) Int. Cl.
*A01H 5/02* (2018.01)
*A01H 6/40* (2018.01)

(52) U.S. Cl.
USPC ..... Plt./433

(58) Field of Classification Search
USPC ..... Plt./433
CPC ..... A01H 5/02; A01H 5/00; A01H 6/40
See application file for complete search history.

(56) References Cited

PUBLICATIONS

Upov Pluto Plant Variety Database Jun. 6, 2021 for *Gentiana* Ashiro 272219, retrieved on Jun. 9, 2021, retrieved from the Internet at https://www.upov.int/pluto/en/index.jsp, 2 pp. (Year: 2021).*

* cited by examiner

*Primary Examiner* — June Hwu
(74) *Attorney, Agent, or Firm* — Penny J. Aguirre

(57) ABSTRACT

A new cultivar of *Gentiana* plant named 'Ashiro 272219' that is characterized by its short plant size and compact plant habit, its flowers with large corollas, its flower lobes and tubes that are white in color and streaked with green and violet-blue, and its long flowering period.

2 Drawing Sheets

Botanical classification: *Gentiana* hybrid.
Varietal denomination: 'Ashiro 272219'.

CROSS REFERENCE TO A RELATED APPLICATIONS

This application is related to a European plant breeders' rights application filed on Jul. 2, 2020, application No. 2020/1610 and to a Japanese plant breeders' rights application filed on Mar. 25, 2020, application No. 34583. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Gentiana* and will be referred to hereafter by its cultivar name, 'Ashiro 272219'. 'Ashiro 272219' represents a new *Gentiana*, an herbaceous perennial grown for landscape and container use.

'Ashiro 272219' arose from crosses made in October 2015 in Hachimantai City, Iwate, Japan by the Inventor between *Gentiana* 'Crystal Ashiro' (not patented) as the female parent and unpatented and unnamed proprietary plants of *Gentiana* from the Inventor's breeding program (a seed strain designated as 25-322KBMS) as the male parent. The seeds were pooled for the crosses and therefore the specific male parent is unknown. 'Ashiro 272219' was selected as a single unique plant in September of 2017 from amongst the seedlings derived from the above crosses.

Asexual propagation of the new cultivar was first accomplished by Inventor by softwood stem tip cuttings in Hachimantai City, Iwate, Japan in January of 2016 for further evaluation. Asexual propagation by softwood stem tip cuttings and tissue culture using meristamic tissue has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Ashiro 272219' as a new and unique cultivar of *Gentiana*.

1. 'Ashiro 272219' exhibits a short plant size and compact plant habit.
2. 'Ashiro 272219' exhibits flowers with large corollas.
3. 'Ashiro 272219' exhibits flower lobes and tubes that are white in color and streaked with green and violet-blue.
4. 'Ashiro 272219' exhibits a long flowering period.

The female parent plant of 'Ashiro 272219' differs from 'Ashiro 272219' in having a taller plant height, corollas that are smaller in size, and a shorter flowering period. 'Ashiro 272219' can be most closely compared to the *Gentiana* cultivars 'Koibeni' (not patented) and 'Lovely Ashiro' (not patented). 'Koibeni' is similar to 'Ashiro 272219' in having single flowers and in being suitable for use as a potted plant. 'Lovely Ashiro' is similar to 'Ashiro 272219' in having single flowers and a similar flowering period. 'Koibeni' differs from 'Ashiro 272219' in having longer stems, smaller corollas, flowers that are purple in color, and a later and shorter flowering period. 'Lovely Ashiro' differs from 'Ashiro 272219' in having flowers that are lilac purple in color and corollas that are smaller in diameter.

BRIEF DESCRIPTION OF THE DRAWINGS

The accompanying color photographs illustrate the overall appearance and distinct characteristics of the new *Gen-*

*tiana*. The photographs were taken of plants 16 months in age as grown in a half-open greenhouse in Hachimantai City, Iwate, Japan.

Figure 1:
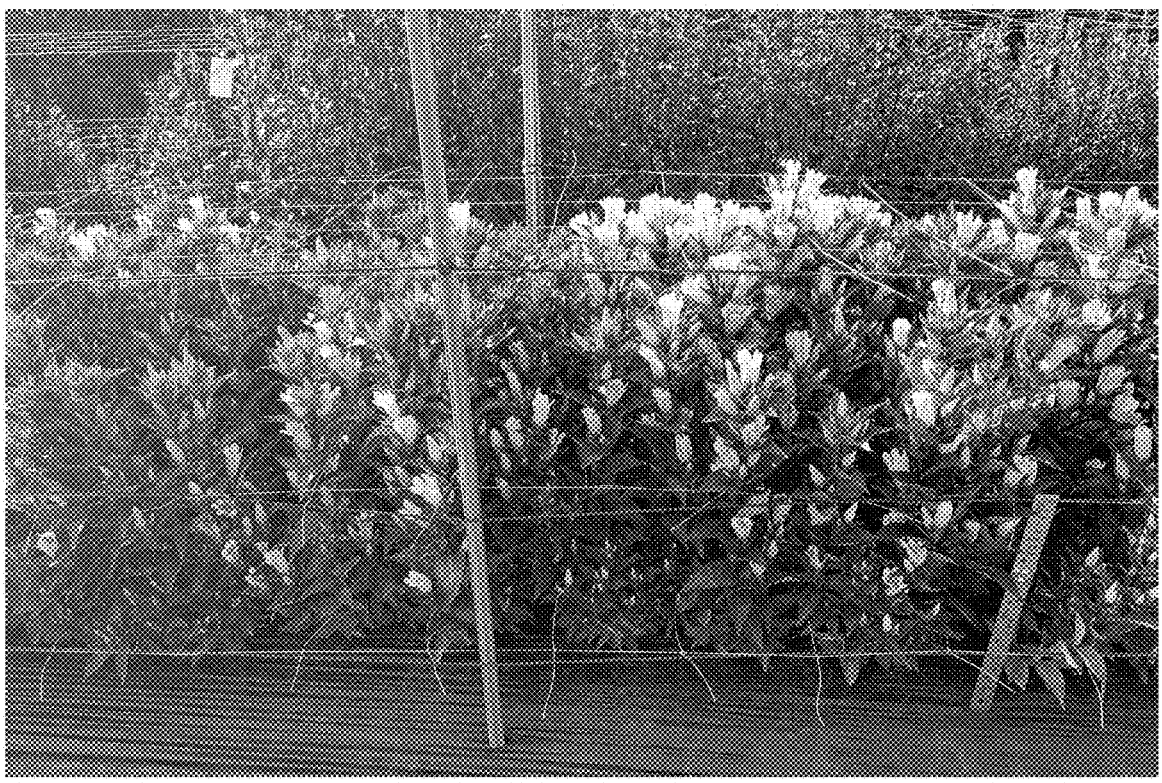
FIG. 1 provides a side view of the flowering plants of 'Ashiro 272219'.
Figure 2:
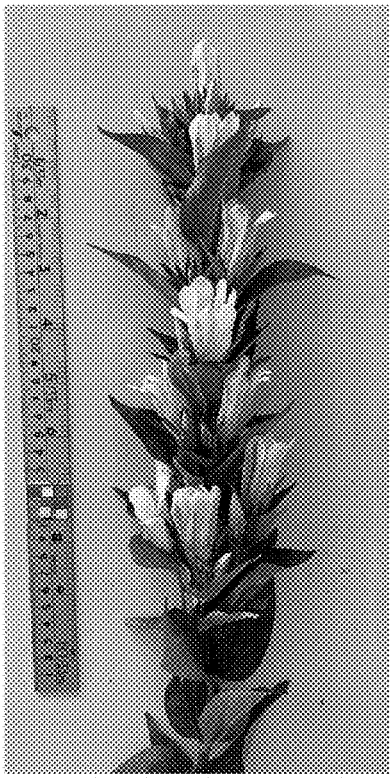

The photograph in FIG. 2 provides a close-up view of the flowers of 'Ashiro 272219'.

Figure 3:
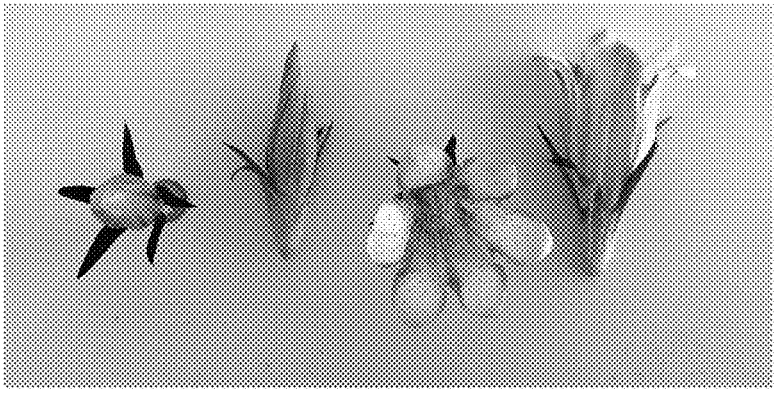

The photograph in FIG. 3 provides a close-up view of a flower buds and flowers of 'Ashiro 272219'.

The colors in the photographs are as close as possible with the photographic and printing technology utilized and the color values cited in the detailed botanical description accurately describe the colors of the new *Gentiana*.

DETAILED BOTANICAL DESCRIPTION OF THE PLANT

The following is a detailed description of plants 16 months in age as grown in a half-open greenhouse in Boskoop, the Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From mid-September to early October in Japan.

*Plant type*.—Herbaceous perennial.

*Plant habit*.—Upright, narrow obovate, compact and short.

*Height and spread*.—An average of 15 cm in height (soil level to top of foliar plane), 17.8 cm in height (soil level to top of floral plane) and 15.7 cm in width.

*Hardiness*.—At least in U.S.D.A. Zones 6 to 10.

*Diseases and pests*.—No susceptibility or resistance to diseases or pests has been observed.

*Root description*.—Fine and fibrous.

*Propagation type*.—Softwood stem tip cuttings and tissue culture.

*Root development*.—An average of 6 months to fully root in a container from a tissue culture plug.

*Growth rate*.—Moderate to low.

Stem description:

*Stem shape*.—Rounded.

*Stem color*.—Young; 145B, mature; 144A to 144B with lower ⅔ moderately suffused with anthocyanin 187A in color.

*Stem size*.—An average of 10.4 cm in length and 3 mm in diameter.

*Stem surface*.—Moderately glossy.

*Stem aspect*.—Average angle of 15°.

*Internode length*.—An average of 1.7 cm with an average of 1 internodes per stem longer than 5 cm.

*Position of longest leaf*.—In central third.

*Branching habit*.—Main branches grow from base with lateral branches, an average of 3 main basal stems and 1 lateral branches per main stem.

*Side shoots*.—An average of 4 side shoots; few with one node and many with more than one node.

Foliage description:

*Leaf shape*.—Ovate.

*Leaf division*.—Simple.

*Leaf base*.—Truncate.

*Leaf apex*.—Acute.

*Leaf venation*.—Parellel, upper surface 144B and 144C, lower surface 147D, only the mid rib on upper surface is conspicuous.

*Leaf margins*.—Entire.

*Leaf twisting*.—Slightly present.

*Leaf attachment*.—Sessile.

*Leaf arrangement*.—Opposite.

*Leaf surface*.—Upper and lower surface; smooth, glabrous and slightly glossy.

*Leaf color*.—Young upper surface; 137A, young lower surface; 146B, mature upper surface; between NN137A and 147A, mature lower surface; 146B, anythocyanin is absent.

*Leaf number*.—Average of 30 (15 pairs) per main stem.

*Leaf size*.—Average of 6 cm in length and 3.2 cm in width.

Flower description:

*Flower type*.—Axillary and terminal tubular flowers, solitary.

*Flower fragrance*.—None.

*Flower lastingness*.—Average of 10 days on plant, persistent.

*Flowering sequence*.—Flowering on terminus and axillary nodes is primarily simultaneous.

*Flower buds*.—Oblanceolate in shape, average of 2.6 cm in diameter (including sepals), 1.2 cm in diameter (excluding sepals) and 5.3 mm in length, surface is smooth, glabrous and matte, color; 145B, top 145C, base 145D, axially striped (5 stripes) 94C, immature sepals 139A, calyx 145C.

*Flower quantity*.—An average of 20 per stem.

*Flower aspect*.—Held upright.

*Flower shape*.—Tubular.

*Flower size*.—An average of 3.7 cm in diameter and 5.9 cm in length, throat diameter 1.8 cm, flower tube length 4.8 cm, flower tube diameter 2.2 cm.

*Pedicels*.—None present.

*Peduncles*.—An average of 2 mm in length and 3 mm in width, held upright on terminal flowers and an average angle of 35° to vertical for axillary flowers, strong, smooth, glabrous and slightly glossy surface, 145B in color.

*Petal description*.—6, occasionally 5, oblong in shape, an average of 6 cm in length and 1.15 cm in width, 86.5% of lower portion is fused into a tubular shape, margin is entire, apex is broadly acute with a mucronulate tip, lobes are reflexed, upper and lower surface is glabrous, smooth and velvety in appearance, color opening and fully open inner and outer surface; NN155D, outer surface of lobes are sparsely covered with fine dots 143A and streaked with 143C, inner surface of lobes is moderately covered with fine dots 143A with lower margins 94D, throat color; NN155B, sparsely covered with fine dots 143A, tube color; inner surface 157C to 157D, densely covered with fine dots 143B, axially striped 96D and 145C, outer surface; 157B, sparsely covered with fine dots 143B, axially striped 94D and 145C.

*Paracorolla*.—Absent.

*Calyx form*.—Campanulate, 3.6 cm in length, 3.1 cm in diameter.

*Sepals*.—Rotate, fused into a campanulate shape, an average of 5, occasionally 6, average of 3.2 cm in length and 3.5 mm in width, narrow oblong in shape, margin is entire, apex is free and acute, base is fused, upper 55% free, upper and lower surface is smooth and slightly glossy, color; when opening upper surface 139A, lower 55% 145C, when opening lower surface 145A, lower 55% 145B to 145C, fully open upper surface 139A, lower 55% 145C, fully open lower surface 146B, lower 55% 145B.

Reproductive organs:

*Gynoecium*.—Pistil; 1, 5 mm in length, stigma; 1.5 mm in diameter, decurrent, split in two, 151D in color, style; 1.5 mm in length, 157D in color, ovary; 147D, lower half 145B in color.

*Androecium*.—Stamens; 5, filaments; 3.3 cm in length, 157C to 157D in color, anther; dorsifixed, elliptic in shape, 4 mm in length, 1.75 mm in width, 4D in color, pollen; moderate in quantity, 2B to 2C in color.

*Fruit and seed*.—None have been observed to date.

It is claimed:

1. A new and distinct cultivar of *Gentiana* plant named 'Ashiro 272219' as herein illustrated and described.

* * * * *